United States Patent [19]

Marhold

[11] Patent Number: 5,082,971
[45] Date of Patent: Jan. 21, 1992

[54] TRIFLUOROMETHYLAMINOBENZENES CONTAINING FLUORINE AND/OR CHLORINE AND THEIR PREPARATION

[75] Inventor: Albrecht Marhold, Leverkusen, Fed. Rep. of Germany

[73] Assignee: Bayer Aktiengesellschaft, Leverkusen, Fed. Rep. of Germany

[21] Appl. No.: 487,339

[22] Filed: Mar. 1, 1990

Related U.S. Application Data

[63] Continuation of Ser. No. 261,795, Oct. 24, 1988, abandoned.

[30] Foreign Application Priority Data

Nov. 9, 1987 [DE] Fed. Rep. of Germany ....... 3737986

[51] Int. Cl.$^5$ .................. C07C 211/47; C07C 211/46
[52] U.S. Cl. .................................. 564/442; 564/305
[58] Field of Search .......................................... 564/442

[56] References Cited

U.S. PATENT DOCUMENTS 3,148,217  9/1964  Freyermuth et al. ............... 564/417

FOREIGN PATENT DOCUMENTS 0034402  8/1981  European Pat. Off. .
0138359  4/1985  European Pat. Off. .
2812169  10/1978  Fed. Rep. of Germany .
WO8300331  2/1983  PCT Int'l Appl. .
1588111  4/1981  United Kingdom .

Primary Examiner—Glennon H. Hollrah
Attorney, Agent, or Firm—Sprung Horn Kramer & Woods

[57] ABSTRACT

Trifluoromethylaminobenzenes containing fluorine and/or chlorine, in which the trifluoromethyl groups are situated in the 1-position, the amino group
a) is situated in the 2-position and a fluorine atom is situated in the 6-position or two fluorine atoms are situated in the 5- and 6-position or a fluorine atom is situated in the 5-position and a chlorine atom is situated in the 6-position or
b) is situated in the 3-position and a fluorine atom is situated in the 2-position or two fluorine atoms are situated in the 2- and 6-position or a chlorine atom is situated in the 2-position and a fluorine atom is situated in the 6-position or
c) is situated in the 4-position and a fluorine atom is situated in the 2-position and additionally a further fluorine atom is situated in the 3- or 6-position or two further fluorine atoms are situated in the 5- and 6-position or a further fluorine atom is situated in the 6-position and two chlorine atoms are situated in the 3- and 5-position or a chlorine atom is situated in the 3-position to two chlorine atoms are situated in the 3- and 5-position or
d) is situated in the 4-position and two fluorine atoms are situated in the 3- and 5-position or two chlorine atoms are situated in the 2- and 3-position or a fluorine atom is situated in the 3-position and a chlorine atom is situated in the 5-position or
e) is situated in the 2-, 3- or 4-position and three fluorine atoms are situated on the aromatic ring and a process for their preparation.

4 Claims, No Drawings

TRIFLUOROMETHYLAMINOBENZENES CONTAINING FLUORINE AND/OR CHLORINE AND THEIR PREPARATION

This is a continuation of application Ser. No. 07/261,795, filed 10/24/88, now abandoned.

The present invention relates to new compounds from the series comprising trifluoromethylaminobenzenes containing fluorine and/or chlorine and a process for their preparation.

Until now, only a few compounds from the series comprising trifluoromethylaminobenzenes containing fluorine and/or chlorine have been disclosed, for example 2,5-difluoro-3-amino-benzotrifluoride, 2-chloro-3-amino-5-fluoro-benzotrifluoride, 2-fluoro-3-amino-5-chloro-benzotrifluoride and 2,5,6-trifluoro-3-chloro-4-aminobenzotrifluoride (see EP-OS 0,138,359, U.S. Pat. No. 4,275,210, DE-OS (German Published Specification) 2,812,169 and Zh. Obshch. Khim. 33 (7), 2358–64 (1963)).

Some of these known trifluoromethylaminobenzenes containing fluorine and/or chlorine are only accessible in a very complicated manner in a multi-stage process, other compounds of this type have hitherto not been described at all.

2-Amino-4-fluoro-benzotrifluoride can be prepared, for example, by chlorinating 4-fluorophthalic anhydride with phosphorus pentachloride, subsequently fluorinating with antimony trifluoride, converting the trifluoromethylfluoro-benzoyl fluoride obtained into the corresponding amide and obtaining the corresponding aniline from this by Hofmann degradation using hypobromite (see Zh. Obshch. Khim. 33 (7), 2358–64 (1963)). The multi-stage procedure is disadvantageous.

This process cannot be transferred to the preparation of other trifluoromethylaminobenzenes containing fluorine and/or chlorine, since altered substitution patterns mean changed reactivities.

New trifluoromethylaminobenzenes containing fluorine and/or chlorine have now been found in which the trifluoromethyl group is situated in the 1-position and the amino group a) is situated in the 2-position and a fluorine atom is situated in the 6-position or two fluorine atoms are situated in the 5- and 6-position or a fluorine atom is situated in the 5-position and a chlorine atom is situated in the 6-position or b) is situated in the 3-position and a fluorine atom is situated in the 2-position or two fluorine atoms are situated in the 2- and 6-position or a chlorine atom is situated in the 2-position and a fluorine atom is situated in the 6-position or c) is situated in the 4-position and a fluorine atom is situated in the 2-position and additionally a further fluorine atom is situated in the 3- or 6-position or two further fluorine atoms are situated in the 5- and 6-position or a further fluorine atom is situated in the 6-position and two chlorine atoms are situated in the 3- and 5-position or a chlorine atom is situated in the 3-position or two chlorine atoms are situated in the 3- and 5-position or d) is situated in the 4-position and two fluorine atoms are situated in the 3- and 5-position or two chlorine atoms are situated in the 2- and 3-position or a fluorine atom is situated in the 3-position and a chlorine atom is situated in the 5-position or e) is situated in the 2-, 3- or 4-position and three fluorine atoms are situated on the aromatic ring.

In detail, the compounds of the preceding sections a) to d) are 2-amino-6-fluoro-benzotrifluoride, 2-amino-5,6-difluoro-benzotrifluoride, 2-amino-5-fluoro-6-chloro-benzotrifluoride, 2-fluoro-3-amino-benzotrifluoride, 2,6-difluoro-3-amino-benzotrifluoride, 2-chloro-3-amino-6-fluoro-benzotrifluoride, 2,3-difluoro-4-amino-benzotrifluoride, 2,6-difluoro-4-amino-benzotrifluoride, 2,5,6-trifluoro-4-amino-benzotrifluoride, 2,6-difluoro-3,5-dichloro-4-amino-benzotrifluoride, 2-fluoro-3-chloro-4-amino-benzotrifluoride, 2-fluoro-3,5-dichloro-4-amino-benzotrifluoride, 3,5-difluoro-4-amino-benzotrifluoride, 2,3-dichloro-4-amino-benzotrifluoride and 3-fluoro-4-amino-5-chloro-benzotrifluoride. From the compounds from section e) may be mentioned, for example, 2,5,6-trifluoro-4-amino-benzotrifluoride, 3-amino-4,5,6-trifluoro-benzotrifluoride and 2,4,6-trifluoro-3-amino-benzotrifluoride.

Of these compounds, 2-amino-6-fluoro-benzotrifluoride, 2-fluoro-3-amino-benzotrifluoride, 2,6-difluoro-3-amino-benzotrifluoride, 2,3-difluoro-4-amino-benzotrifluoride, 2,6-difluoro-4-amino-benzotrifluoride, 3,5-difluoro-4-amino-benzotrifluoride, 3-fluoro-4-amino-5-chloro-benzotrifluoride and 2,5,6-trifluoro-4-amino-benzotrifluoride are preferred.

The present invention also relates to the preparation of the trifluoromethylaminobenzenes containing fluorine and/or chlorine according to the invention.

A preferred process for the preparation of trifluoromethylaminobenzenes containing fluorine and/or chlorine, in which the trifluoromethyl group is situated in the 1-position and the amino group a) is situated in the 2-position and a fluorine atom is situated in the 6-position or two fluorine atoms are situated in the 5- and 6-position or a fluorine atom is situated in the 5-position and a chlorine atom is situated in the 6-position or b) is situated in the 3-position and a fluorine atom is situated in the 2-position or two fluorine atoms are situated in the 2- and 6-position or a chlorine atom is situated in the 2-position and a fluorine atom is situated in the 6-position or c) is situated in the 4-position and a fluorine atom is situated in the 2-position and additionally a further fluorine atom is situated in the 3- or 6-position or two further fluorine atoms are situated in the 5- and 6-position or a further fluorine atom is situated in the 6-position and two chlorine atoms are situated in the 3- and 5-position or a chlorine atom is situated in the 3-position or two chlorine atoms are situated in the 3- and 5-position or d) is situated in the 4-position and two fluorine atoms are situated in the 3- and 5-position or two chlorine atoms are situated in the 2- and 3-position or a fluorine atom is situated in the 3-position and a chlorine atom is situated in the 5-position or e) is situated in the 2-, 3- or 4-position and three fluorine atoms are situated on the aromatic ring, is characterized in that corresponding trifluoromethylbenzenes containing fluorine and/or chlorine are nitrated and the fluorine and/or chlorine-containing trifluoromethylnitrobenzenes thus obtained are reduced.

The trifluoromethylbenzenes containing fluorine and/or chlorine, but free of amino groups, to be employed in this process according to the invention are known (see, for example, J. Chem. Soc. C, (8)

1547-1549 (1971) and Can. J. Chem. 57 (7), 807-812 (1979)).

The nitration can be carried out using customary nitrating agents, for example with mixtures of nitric and sulphuric acid. The temperature, in this process can be, for example, in the range from 0° to 80° C., preferably it is 20° to 50° C. The nitrating agents can be employed, for example, in amounts in which 0.8 to 1.5 moles of nitrating agent per mole of starting compound are formed in the reaction mixture. Preferably, sufficient nitrating agent is employed to form 1 to 1.1 moles of nitrating agent per mole of starting compound. The nitration can be carried out, if desired, in the presence of an inert organic solvent. Methylene chloride, for example, is suitable.

The reduction following this can be carried out chemically, i.e. for example using reducing metals or metal salts. Iron, zinc, tin, tin(II) chloride and titanium-(III) chloride, for example, are suitable. Reductants of this type are preferably employed in the stoichiometrically required amount. For a reduction of this type, the nitro compounds can be employed, for example, in the form in which they are produced in the nitration or in purified form.

The reduction can also be carried out catalytically using hydrogen, where, for example, catalysts can be employed which contain metals or consist thereof. Metals of sub-group VIII of the periodic table of the elements, in particular palladium, platinum and nickel, for example, are suitable. The metals can be present in elementary form or in the form of compounds, and also in particularly activated forms, for example in the form of Raney metals or as a metal or metal compound applied to support materials. Raney nickel, palladium on carbon and palladium on aluminium oxide are preferred.

The catalytic reduction is preferably carried out in the presence of a solvent. Alcohols and ethers, such as methanol, ethanol and tetrahydrofuran, for example, are suitable. The catalytic reduction can be carried out, for example, at temperatures in the range 10° to 60° C. and, for example, at hydrogen pressures in the range 1 to 100 bar. Excesses of hydrogen are in general not critical.

Acid-free nitro compounds are preferably employed for the catalytic reduction. According to the preparation, they therefore have to be freed from acids, if necessary, for example by washing with water or neutralizing with a base.

The working-up of the reaction mixture present after chemical reduction or catalytic hydrogenation can be carried out, for example, by first filtering off possible solid components present and distilling the filtrate, if necessary after a wash with water. If a mixture of isomers is produced as a reaction product, these can optionally be separated by precision distillation.

In a variation of the previously described catalytic reduction, the reaction is carried out in the presence of a base, for example in the presence of hydroxides or carbonates of alkali metals or tertiary amines. Tertiary amines such as triethylamine or pyridine are preferred. Using one equivalent of base in each case per mole of the nitro compound employed in the catalytic reduction, one equivalent of chlorine atoms can additionally be eliminated from the latter during catalytic reduction. A chlorine-free, fluorine-containing aminobenzotrifluoride can thus be obtained, for example, from a nitrobenzotrifluoride containing fluorine and chlorine.

A further process specific to the preparation of trifluoromethylaminobenzenes, containing fluorine and-/or chlorine in which the trifluoromethyl group is situated in the 1-position and the amino group a') is situated in the 2-position and a fluorine atom is situated in the 6-position or two fluorine atoms are situated in the 5- and 6-position or a fluorine atom is situated in the 5-position and a chlorine atom is situated in the 6-position or b') is situated in the 4-position and a fluorine atom is situated in the 2-position and additionally a further fluorine atom is situated in the 3- or 6-position or two further fluorine atoms are situated in the 5- and 6-position or a further fluorine atom is situated in the 6-position and two chlorine atoms are situated in the 3- and 5-position or a chlorine atom is situated in the 3-position or two chlorine atoms are situated in the 3- and 5-position or c') is situated in the 4-position and two fluorine atoms are situated in the 3- and 5-position or two chlorine atoms are situated in the 2- and 3-position or a fluorine atom is situated in the 3-position and a chlorine atom is situated in the 5-position or d') is situated in the 2- or 4-position and three fluorine atoms are situated on the aromatic ring is characterized in that corresponding fluorine and/or chlorine-containing, 2- and/or 4-halogeno-trifluoromethylbenzenes are reacted with ammonia at elevated pressure in the presence of an organic solvent.

The 2- and/or 4-halogeno-trifluoromethylbenzenes to be employed in this process are known (see Izv. Sib. Otd. Akad. Nauk. SSSR, Ser. Khim. Nauk., (2), 133-141 (1977)). They are preferably 2- and/or 4-chloro-trifluoromethylbenzenes or 2- and/or 4-fluoro-trifluoromethylbenzenes.

The ammonia can be added in liquid or gaseous form, for example in substance (gaseous or liquid) or as an aqueous solution. 1 to 10 moles of ammonia can be used, for example, per mole of halogen atoms to be replaced in the 2- and/or 4-position by $NH_2$ groups. This amount is preferably 3 to 8 moles. Suitable temperatures for this reaction are, for example, those in the range from 80° to 160° C., those in the range 100° to 130° C. being preferred. The reaction can be carried out under the intrinsic pressure of the ammonia adjusted in the closed vessel at reaction temperature which, for example, can be in the range from 10 to 20 bar. Higher pressures can also be used, for example those up to 100 bar.

Inert or substantially inert organic solvents of the most diverse types can be employed as solvent for this reaction. Those suitable, for example, are: alcohols, ethers, sulphones and aromatic hydrocarbons.

The desired reaction products can be obtained, for example, from the reaction mixture present after the reaction by first cooling and releasing the pressure, then removing the solvent and subsequently carrying out a distillation, preferably under reduced pressure.

The trifluoromethylaminobenzenes containing fluorine and/or chlorine according to the invention are useful intermediates. For example, they can be reacted with acrylonitrile under diazotization conditions, α-chloro-β-phenylpropionitriles can thus be obtained, the phenyl moiety of which (with the exception of the $NH_2$ group) is substituted in the same manner as in the product according to the invention employed in each case, this can be converted by dehydrohalogenation into the corresponding cinnamonitrile and 3-cyano-4-phenyl-pyrroles can be obtained therefrom by reaction with sulphonylmethyl isocyanides, the phenyl moiety of which (with the exception of the NH$_2$ group) is substituted in the same manner as in the product according to the invention employed in each case. 3-Cyano-4-phenyl-pyrroles of this type have a particularly good activity as fungicides, in particular for the protection of plants against Plasmodiophoromycetes, Oomycetes, Chrytridiomycetes, Zygomycetes, Ascomycetes, Basidiomycetes and Deuteromycetes.

Such 3-cyano and 4-phenyl-pyrroles, their preparation and their use as pesticides are embraced by separate patent applications by the parent company.

EXAMPLES

EXAMPLE 1 a) 220 g of nitrating acid (33% by weight nitric acid, 67% by weight sulphuric acid) were added dropwise at 50° to 55° C. to 162 g of 2,6-difluoro-benzotrifluoride. After a further reaction time of one hour, the mixture was poured onto ice, and the organic phase was separated off using dichloromethane and distilled after drying. 178 g of 3-nitro-2,6-difluoro-benzotrifluoride having a boiling point of 96° to 100° C. at 22 mbar and a refractive index $n_D^{20}$ of 1.4570 were obtained.

b) 178 g of the nitro compound obtained according to a) in 680 ml of tetrahydrofuran were initially introduced into a hydrogenation apparatus together with 15 g of Raney nickel and the mixture was hydrogenated at 25° to 45° C. using a hydrogen pressure of 30 to 50 bar. When no more hydrogen was taken up, the mixture was cooled and the pressure was released. 147 g of 2,6-difluoro-3-amino-benzotrifluoride having a boiling point of 89° to 90° C. at 18 mbar were obtained by distillation of the filtered reaction mixture.

EXAMPLE 2

200 ml of tetrahydrofuran and 50 g of 2,4,6-trifluorobenzotrifluoride were initially introduced into a stainless steel autoclave and it was pressurized using 30 ml of liquid ammonia. Subsequently, the mixture was heated at 120° C. for 6 hours with stirring. After cooling and releasing the pressure, the reaction mixture was subjected to a fractional distillation. 15 g of 2-amino-4,6-difluoro-benzotrifluoride were obtained at a boiling point of 57° to 58° C. at 12 mbar. After a small intermediate run, 32 g of 2,6-difluoro-4-amino-benzotrifluoride passed over at a boiling point of 103° to 105° C. at 16 mbar. The melting point of the 2,6-difluoro-4-amino-benzotrifluoride obtained was 66° C.

EXAMPLE 3

500 g of 3,4,5-trifluoro-benzotrifluoride were initially introduced into a stainless steel autoclave, 2000 ml of tetrahydrofuran were added and it was pressurized using 150 g of liquid ammonia. The autoclave was heated at 120° to 130° C. for 5 hours with stirring, then cooled and the pressure released at 20° C. In addition to the solvent and starting material, 272 g of 3,5-difluoro-4-aminobenzotrifluoride having a boiling point of 58° to 60° C. at 16 mbar were obtained by distillation.

EXAMPLE 4

200 g of 2,3,4-trifluorobenzotrifluoride in 500 ml of tetrahydrofuran were initially introduced into an autoclave and it was pressurized using 60 ml of liquid ammonia. After stirring for 6 hours at 130° C. (maximum pressure 18 bar), the mixture was cooled and the pressure was released. By distillation, 72 g of 2-amino-3,4-difluoro-benzotrifluoride were obtained with a boiling point of 60° to 64° C. at 26 mbar and 92 g of 2,3-difluoro-4-amino-benzotrifluoride with a boiling point of 92° to 93° C. at 26 mbar.

EXAMPLE 5

100 g of 2,6-difluorobenzotrifluoride in 300 ml of tetrahydrofuran were initially introduced into a stainless steel autoclave and it was pressurized using 30 ml of liquid ammonia. After stepwise heating to 125° C., the autoclave was stirred at this temperature for 5 hours. After cooling to 20° C., the pressure was released and the solution was distilled under reduced pressure. 46 g of 2-amino-6-fluoro-benzotrifluoride passed over at a boiling point of 49° to 50° C. at 8 mbar.

EXAMPLE 6 a) 100 g of 2-fluoro-5-chloro-benzotrifluoride were initially introduced into a stirring apparatus and 120 g of nitrating acid (33% by weight nitric acid and 67% by weight sulphuric acid) were added dropwise at 40° C. The mixture was stirred for one hour at 40° to 45° C., then cooled and poured onto ice. The organic phase was extracted using dichloromethane, dried and distilled. 112 g of nitro compounds which contained 91.3% by weight of 2-fluoro-5-chloro-3-nitro-benzotrifluoride passed over at a boiling point of 92° to 94° C. at 18 mbar.

b) 111 g of the nitro compounds obtained according to a) in 500 ml of tetrahydrofuran were initially introduced into a hydrogenation apparatus and 50 g of triethylamine and 15 g of Raney nickel were successively added. After flushing the apparatus with hydrogen, the mixture was hydrogenated at 25° to 120° C. using a hydrogen pressure of 30 to 80 bar. After completion of hydrogen uptake, the mixture was cooled and the pressure was released. The reaction mixture was filtered, washed with tetrahydrofuran and most of the tetrahydrofuran was distilled off from the combined filtrates at atmospheric pressure via a column. The residue was stirred with 200 ml of water, then the organic phase was separated off, dried and subjected to a precision distillation under reduced pressure. 52 g of 2-fluoro-3-amino-benzotrifluoride passed over at a boiling point of 70° to 72° C. at 16 mbar.

EXAMPLE 7

110 g of 2,3,4,6-tetrafluoro-benzotrifluoride in 200 ml of tetrahydrofuran were initially introduced into a 0.7 l stainless steel autoclave and it was pressurized using 30 ml of liquid ammonia. The mixture was subsequently heated at 100° C. for 3 hours, a maximum pressure of 10 bar being adjusted. After cooling, the pressure was released and the liquid phase was subjected to a fractional distillation. 42 g of 2-amino-3,4,6-trifluorobenzotrifluoride were first obtained with a boiling point of 47° to 48° C. at 8 mbar, then after an intermediate run, 46 g of 2,5,6-trifluoro-4-amino-benzo-trifluoride with a boiling point of 75° to 78° C. at 8 mbar.

EXAMPLE 8 a) 40 g of 2,3,4-trifluorobenzotrifluoride at 30° C. were initially introduced into a glass stirring apparatus and 45 g of mixed acid (33% by weight of nitric acid, 67% by weight of sulphuric acid) were added dropwise. The mixture was subsequently stirred for 1 hour at 30° C. and for a further hour at 40° C., then a further 30 ml of the mixed acid were added and it was stirred again for a further 2 hours at 60° C. The mixture was then cooled and the batch was poured onto ice, and the organic phase was taken up with dichloromethane, separated off and dried. Fractional distillation yielded 35 g of 2,3,4-trifluoro-5-nitro-benzotrifluoride at 60° to 62° C. at 10 mbar.

b) 35 g of 2,3,4-trifluoro-5-nitro-benzotrifluoride in 150 ml of tetrahydrofuran were initially introduced into a hydrogenation apparatus, 3 g of Raney nickel were added and, after flushing with nitrogen, the mixture was hydrogenated to constant pressure with 30 bar of hydrogen at 25° to 45° C. After completion of the hydrogen uptake, the pressure was released and the reaction solution was filtered and subsequently fractionally distilled. 27 g of 2,3,4-trifluoro-5-amino-benzotrifluoride were obtained with a boiling point of 82° to 83° C. at 15 mbar.

EXAMPLE 9 a) 120 g of nitrating acid (33% by weight nitric acid, 67% by weight sulphuric acid) were added dropwise to 100 g of 2,4,6-trifluoro-benzotrifluoride which had initially been introduced at 30° C. into a glass stirring apparatus. The mixture was stirred for 1 hour at 30° C. and for 1 hour at 40° to 45° C. and then cooled, and the batch was poured onto ice. The organic phase was separated off using dichloromethane and distilled after drying. 98 g of 2,4,6-trifluoro-5-nitro-benzotrifluoride with a refractive index $n_D^{20}$ of 1.4340 passed over at a boiling point of 78° to 80° C. at 20 mbar.

b) The 98 g of 2,4,6-trifluoro-5-nitro-benzotrifluoride obtained previously were dissolved in 400 ml of tetrahydrofuran in a hydrogenation apparatus, and 8 g of Raney nickel were added. The mixture was then hydrogenated to constant pressure with hydrogen at 25° to 45° C. at a pressure of 30 to 50 bar. After releasing the pressure of the excess hydrogen, the reaction solution was filtered and then distilled. 85 g of 2,4,6-trifluoro-5-amino-benzo-trifluoride having a boiling point of 70° C. at 12 mbar and a refractive index $n_D^{20}$ of 1.4330 were obtained.

EXAMPLE 10

225 g of 2,4,5-trifluorobenzotrifluoride in 600 ml of tetrahydrofuran were initially introduced into an autoclave and it was pressurized using 100 ml of liquid ammonia. The mixture was heated at 140° C. for 8 hours with stirring at 400 rpm and then cooled to 20° C. After releasing the pressure of the unused ammonia, the batch was distilled. 37 g of 4,5-difluoro-2-aminobenzotrifluoride were obtained in the forerun. The main amount distilled at 78° C./18 mbar and is, according to NMR spectroscopic findings, 2,5-difluoro-4-amino-benzotrifluoride ($n_D^{20}$: 1.4560) having a yield of 154 g.

What is claimed is:

1. A trifluoromethylaminobenzene containing at least one fluorine situated on the benzene ring wherein the trifluoromethyl group is situated in the 1-position and the amino group
    a) is situated in the 2-position and a fluorine atoms is situated in the 6-position or two fluorine atoms are situated in the 5- and 6-positions or a fluorine atom is situated in the 5-position and a chlorine atom is situated in the 6-position or
    b) is situated in the 3-position and a fluorine atom is situated in the 2- and 6-positions or a chlorine atom is situated in the 2-position and a fluorine atom is situated in the 6-position or
    c) is situated in the 4-position and a fluorine atom is situated in the 2-position and additionally a further fluorine atom is situated in the 3- or 6-position or two further fluorine atoms are situated in the 5- and 6-positions or a further fluorine atom is situated in the 6-position and two chlorine atoms are situated in the 3- and 5-positions or a chlorine atom is situated in the 3-position or two chlorine atoms are situated in the 3- and 5-positions or
    d) is situated in the 4-position and two fluorine atoms are situated in the 3- and 5-positions or a fluorine atom is situated in the 3-position and a chlorine atom is situated in the 5-position or
    e) is situated in the 2-, 3- or 4-position and three fluorine atoms are situated on the aromatic ring.

2. A trifluoromethylaminobenzene according to claim 1, wherein the trifluoromethylaminobenzene is selected from the group consisting of 2-amino-6-fluoro-benzotrifluoride, 2-amino-5,6-difluoro-benzotrifluoride, 2-amino-5-fluoro-6-chloro-benzotrifluoride, 2-fluoro-3-amino-benzotrifluoride, 2,6-difluoro-3-amino-benzotrifluoride, 2-chloro-3-amino-6-fluoro-benzotrifluoride, 2,3-difluoro-4-amino-benzotrifluoride, 2,6-difluoro-4-amino-benzotrifluoride, 2,5,6-trifluoro-4-amino-benzotrifluoride, 2,6-difluoro-3,5-dichloro-4-amino-benzotrifluoride, 2-fluoro-3-chloro-4-amino-benzotrifluoride, 2-fluoro-3,5-dichloro-4-amino-benzotrifluoride, 3,5-difluoro-4-amino-benzotrifluoride, 3-fluoro-4-amino-5-chlorobenzotrifluoride, 2,5,6-trifluoro-4-amino-benzotrifluoride, 4-amino-4,5,6-trifluoro-benzotrifluoride and 2,4,6-trifluoro-3-amino-benzotrifluoride.

3. A trifluoromethylaminobenzene according to claim 1, wherein the trifluoromethylaminobenzene is 2-fluoro-3-amino-benzotrifluoride.

4. A trifluoromethylaminobenzene according to claim 1, wherein the trifluoromethylaminobenzene is 2,3-difluoro-4-amino-benzotrifluoride.

* * * * *